United States Patent [19]

Krapcho et al.

[11] 3,960,848

[45] June 1, 1976

[54] 2-AMINOALKYL-3A,4,5,6,7,8-HEXAHYDRO-3-PHENYL-8-(PHENYLME-THYLENE)-CYCLOPENTA[C]PYRAZOLES

[75] Inventors: John Krapcho, Somerset; Chester Frank Turk, Kendall Park, both of N.J.

[73] Assignee: E. R. Squibb & Sons, Inc., Princeton, N.J.

[22] Filed: June 30, 1975

[21] Appl. No.: 591,544

Related U.S. Application Data

[63] Continuation-in-part of Ser. No. 469,171, May 13, 1974, abandoned.

[52] U.S. Cl. .................... 260/240 F; 260/250 AC
[51] Int. Cl.² ........................................ C07D 231/54
[58] Field of Search ............... 260/240 F, 250 AC

[56] References Cited
UNITED STATES PATENTS

| | | | |
|---|---|---|---|
| 3,205,230 | 9/1965 | Pribyl et al. | 260/250 AC |
| 3,852,279 | 12/1974 | Krapcho et al. | 260/240 F |

*Primary Examiner*—Allen B. Curtis
*Attorney, Agent, or Firm*—Lawrence S. Levinson; Merle J. Smith; Stephen B. Davis

[57] ABSTRACT

Compounds of the following formula and their acid-addition and quaternary salts and N-oxides

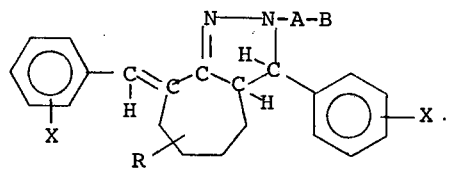

wherein X is hydrogen, chloro, fluoro, trifluoromethyl, lower alkyl, or lower alkoxy, R is hydrogen or lower alkyl, A is alkylene of 1 to 8 carbons, and B is $-NH_2$,

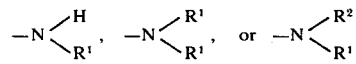

wherein $R^1$ is lower alkyl and $R^2$ is phenyl or phenyl-lower alkyl are disclosed. These compounds are useful as central nervous system depressants.

6 Claims, No Drawings

2-AMINOALKYL-3A,4,5,6,7,8-HEXAHYDRO-3-PHENYL-8-(PHENYLMETHYLENE)-CYCLOPENTA[C]PYRAZOLES

This application is a continuation-in-part and division of Ser. No. 469,171 filed on May 13, 1974, now abandoned.

SUMMARY OF THE INVENTION

This invention relates to new compounds of the formula (I) 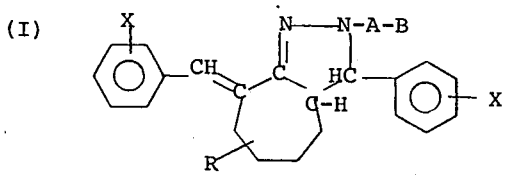

and their acid addition salts, quaternary salts, and N-oxides which are central nervous system depressants.

X represents hydrogen, chloro, fluoro, trifluoromethyl, lower alkyl or lower alkoxy; R represents hydrogen or lower alkyl; A is straight or branched chain alkylene; and B represents $-NH_2$,

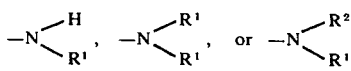

wherein $R^1$ is lower alkyl and $R^2$ is phenyl or phenyl-lower alkyl.

The terms "lower alkyl" and "lower alkoxy" as employed herein include both straight and branched chain radicals of less than eight carbon atoms, preferably 1 to 4 carbon atoms, as for example, methyl, ethyl, propyl, isopropyl, t-butyl, methoxy, ethoxy, propoxy, isopropoxy, n-butoxy, etc. The term "phenyl-lower alkyl" includes such lower alkyl groups attached to a phenyl with benzyl and phenethyl being preferred.

The term "alkylene" as employed herein includes both straight and branched chain radicals of 1 to 8 carbon atoms, as for example, $-(CH_2)-$, $-(CH_2)_2-$,

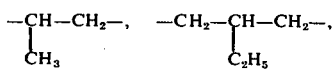

etc.

The term "acid addition salts" is intended to mean salts which may be formed for the purposes of isolation, purification, and storage, such as the oxalate salt, maleate salt, etc. and pharmaceutically acceptable salts meant for administration of the compound to a host, such as the hydrochloride, sulfate, acetate, citrate salts, etc. The quaternary salts include those formed with alkyl halides (e.g. methyl chloride, isobutyl bromide, dodecyl chloride and cetyl iodide), benzyl halides (e.g. benzyl chloride) and dilower alkyl sulfates (e.g. dimethyl sulfate) by a conventional quaternization reaction.

The N-oxide may be formed by dissolving the free base of Formula I in a solvent inert to hydrogen peroxide, e.g., ethanol or chloroform, adding excess (on a molar basis) hydrogen peroxide, and allowing the mixture to stand at room temperature for several hours. An acid-addition salt of the N-oxide may be formed by addition of the desired acid, for example, those mentioned above.

DETAILED DESCRIPTION OF THE INVENTION

The new compounds of formula I are prepared by reacting the appropriate cycloalkylone represented by formula (II) 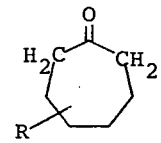

with a substituted benzaldehyde of formula (III) 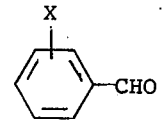

to produce the intermediate of the formula (IV) 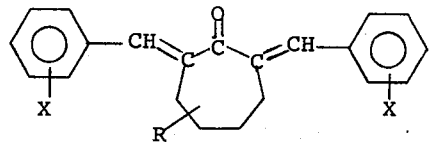

The compounds of formula IV are converted to a compound of formula I by reaction with a hydrazine of formula

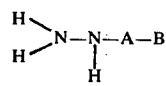 (V)

in an organic solvent, preferably an alcohol of up to four carbon atoms at temperatures of from about 40°C to about 120°C, preferably at about the reflux temperature of the solvent, for from about ½ hour to about 12 hours, preferably for about 4 hours.

The hydrazine of formula V is prepared by reacting a haloamine, B-A-halo, with an excess of hydrazine, $H_2NNH_2$.

Alternatively, the compound of formula IV can be reacted with a hydroxyalkyl hydrazine of formula

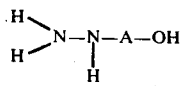 (VI)

to form the alcohol of formula (VII)

The alcohol of formula VII is reacted by heating with p-toluenesulfonyl chloride to form the tosylate of formula (VIII)

which in turn is treated with the amine of formula HB to form the compounds of formula I. This method is particularly useful in producing compounds of formula I where B is amino (i.e. the tosylate of formula VIII is reacted with ammonia).

Preferred are the compounds of formula I wherein
X is hydrogen, lower alkyl of 1 to 4 carbon atoms, lower alkoxy of 1 to 4 carbon atoms, trifluoromethyl, chloro or fluoro.
R is hydrogen or lower alkyl of 1 to 4 carbon atoms.
A is straight or branched chain alkylene of from 2 to 5 carbon atoms.
$R^1$ is lower alkyl of 1 to 4 carbon atoms.
$R^2$ is phenyl, benzyl, or phenethyl.

The most preferred compounds are those wherein
X is hydrogen or Cl, especially hydrogen.
R is hydrogen.
B is $$-N\begin{matrix}R^1\\R^{1'}\end{matrix}$$

especially $-N(CH_3)_2$.
A is $-(CH_2)_2-$ or $-(CH_2)_3-$, especially $-(CH_2)_3$.

The new compounds of the present invention are useful as central nervous system depressants in mice, cats, rats, dogs and other mammalian species when administered in amounts ranging from about 1.0 mg. to about 100 mg. per kg. of body weight per day. A preferred dosage regimen for optimum results would be from about 10 mg. to about 50 mg. per kg. of body weight per day, and such dosage units are employed that a total of from about 35 mg. to about 3 g. of active ingredient in single or divided doses are administered in a 24 hour period. These compounds when administered to rats in the above stated dosages produced the following central nervous system depressant symptoms; decreased motor activity, ataxia, and decreased screen grip.

For these purposes a compound or mixture of compounds of formula I and their pharmaceutically acceptable acidaddition salts, quaternary salts, or N-oxides may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention. All temperatures are expressed on the centigrade scale.

EXAMPLE 1

3a,4,5,6,7,8-Hexahydro-N,N-dimethyl-3-phenyl-8-(phenylmethylene)-cyclohepta[c]pyrazole-2(3H)-propanamine, maleate salt a. 3a,4,5,6,7,8-Hexahydro-N,N-dimethyl-3-phenyl-8-(phenylmethylene)-cyclohepta[c]pyrazole-2(3H)-propanamine, oxalate salt 8.0 g. (0.028 mole) of 2,7-bis(phenylmethylene)cycloheptanone [See Piantadosi et al., J. Med. Chem., 16, 770 (1973)] and 3.4 g. (0.029 mole) of 3-dimethylaminopropylhydrazine are mixed in 70 ml. of methanol, heated and the resulting solution is refluxed for 4 hours. The residue remaining after the evaporation of the methanol is dissolved in 200 cc. of ether, washed six times with 50 ml. portions of water, and dried (MgSO$_4$) and the solvent is evaporated yielding 11.2 g. of oily base.

11.0 g. of this oily base is dissolved in 70 ml. of MeCN and treated with a warm solution of 2.8 g. of oxalic acid in 50 ml. of MeCN. On rubbing and cooling, 13 g. of the oxalate salt slowly separates; m.p. 143°–145° (s. 137°). Crystallization from 25 ml. warm DMF-75 ml. MeCN yields 7.0 g. of cream colored 3a,4,5,6,7,8-hexahydro-N,N-dimethyl-3-phenyl-8-(phenylmethylene)-cyclohepta[c]pyrazole-2(3H)-propanamine, oxalate salt; m.p. 152°–154°.

b. 3a,4,5,6,7,8-Hexahydro-N,N-dimethyl-3-phenyl-8-(phenylmethylene)-cyclohepta[c]pyrazole-2(3H)-propanamine The oxalate salt from part (a) is suspended in water and is basified with K$_2$CO$_3$ and extracted with ether yielding 5.5 g. of oily base. 5.0 g. of this oily base is crystallized from 25 ml. of MeCN yielding 4.4 g. of cream colored 3a,4,5,6,7,8-hexahydro-N,N-dimethyl-3-phenyl-8-(phenylmethylene)-cyclohepta[c]pyrazole-2(3H)-propanamine; m.p. 92°–94° (s. 90°).

c. 3a,4,5,6,7,8-Hexahydro-N,N-dimethyl-3-phenyl-8-(phenylmethylene)-cyclohepta[c]pyrazole-2(3H)-propanamine, maleate salt The base from part (b) and 1.3 g. of maleic acid are dissolved in 25 ml. of warm MeCN and diluted to approximately 600 ml. with ether. On rubbing and standing in the cold, the crystalline maleate salt slowly separates. After four days in the cold, the maleate salt is filtered, washed with ether, and dried in vacuo yielding 4.1 g. (32%); m.p. 109°–111°. Crystallization from 25 ml. methanol-250 ml. ether yields 3.5 g. (27%) of nearly colorless 3a,4,5,6,7,8-hexahydro-N,N-dimethyl-3-phenyl-8-(phenylmethylene)-cyclohepta[c]pyrazole-2(3H)-propanamine, maleate, m.p. 109°–111°.

EXAMPLES 2–10

3a,4,5,6,7,8-Hexahydro-N,N-dimethyl-3-(substituted phenyl)-8-[(substituted phenyl)methylene]-cyclohepta[c]pyrazole-2(3H)-propanamine, maleate salts According to the procedure of example 1 upon substituting for the 2,7-bis(phenylmethylene)cycloheptanone one of the following:

2,7-bis[(2-chlorophenyl)methylene]cycloheptanone
2,7-bis[(3-chlorophenyl)methylene]cycloheptanone
2,7-bis[(4-chlorophenyl)methylene]cycloheptanone
2,7-bis[(4-trifluoromethylphenyl)methylene]cycloheptanone
2,7-bis[(3-fluorophenyl)methylene]cycloheptanone
2,7-bis[(2-methylphenyl)methylene]cycloheptanone
2,7-bis[(4-propylphenyl)methylene]cycloheptanone
2,7-bis[(3-ethoxyphenyl)methylene]cycloheptanone
2,7-bis[(4-propoxyphenyl)methylene]cycloheptanone one obtains the following:

3a,4,5,6,7,8-hexahydro-N,N-dimethyl-3-(2-chlorophenyl)-8-[(2-chlorophenyl)methylene]-cyclohepta[c]pyrazolo-2(3H)-propanamine, maleate salt,
3a,4,5,6,7,8-hexahydro-N,N-dimethyl-3-(3-chlorophenyl)-8-[(3-chlorophenyl)methylene]-cyclohepta[c]pyrazolo-2(3H)-propanamine, maleate salt,
3a,4,5,6,7,8-hexahydro-N,N-dimethyl-3(4-chlorophenyl)-8-[(4-chlorophenyl)methylene]-cyclohepta[c]pyrazolo-2(3H)-propanamine, maleate salt,
3a,4,5,6,7,8-hexahydro-N,N-dimethyl-3-(4-trifluoromethylphenyl)-8-[(4-trifluoromethylphenyl)methylene]-cyclohepta[c]pyrazolo-2(3H)-propanamine, maleate salt,
3a,4,5,6,7,8-hexahydro-N,N-dimethyl-3-(3-fluorophenyl)-8-[(3-fluorophenyl)methylene]-cyclohepta[c]pyrazolo-2(3H)-propanamine, maleate salt,
3a,4,5,6,7,8-hexahydro-N,N-dimethyl-3-(2-methylphenyl)-8-[(2-methylphenyl)methylene]-cyclohepta[c]pyrazolo-2(3H)-propanamine, maleate salt,
3a,4,5,6,7,8-hexahydro-N,N-dimethyl-3-(4-propylphenyl)-8-[(4-propylphenyl)methylene]-cyclohepta[c]pyrazolo-2(3H)-propanamine, maleate salt,
3a,4,5,6,7,8-hexahydro-N,N-dimethyl-3-(3-ethoxyphenyl)-8-[(3-ethoxyphenyl)methylene]-cyclohepta[c]pyrazolo-2(3H)-propanamine, maleate salt, and
3a,4,5,6,7,8-hexahydro-N,N-dimethyl-3-(4-propoxyphenyl)-8-[(4-propoxyphenyl)methylene]-cyclohepta[c]pyrazolo-2(3H)-propanamine, maleate salt.

EXAMPLES 11–17

3a,4,5,6,7,8-Hexahydro-N,N-dimethyl-3-phenyl-(4 and/or 7 or 5 and/or 6-lower alkyl)-8-(phenylmethylene)-cyclohepta[c]pyrazole-2(3H)-propanamine, maleate salts Following the procedure of example 1 but substituting for the 2,7-bis(phenylmethylene)cycloheptanone one of the following:

2,7-bis(phenylmethylene) (4-methylcycloheptanone)
2,7-bis(phenylmethylene) (4-ethylcycloheptanone)
2,7-bis(phenylmethylene) (4-propylcycloheptanone)
2,7-bis(phenylmethylene) (4-t-butylcycloheptanone)
2,7-bis(phenylmethylene) (3-methylcycloheptanone)
2,7-bis(phenylmethylene) (3-ethylcycloheptanone)
2,7-bis[(4-chlorophenyl)methylene](4-methylcycloheptanone)

one obtains the following:

3a,4,5,6,7,8-hexahydro-N,N-dimethyl-5 and/or 6-methyl)-3-phenyl-8-phenylmethylene-cyclohepta[c]pyrazole-2(3H)-propanamine, maleate salt,
3a,4,5,6,7,8-hexahydro-N,N-dimethyl-(5 and/or 6-ethyl)-3-phenyl-8-phenylmethylene-cyclohepta[c]pyrazole-2(3H)-propanamine, maleate salt,
3a,4,5,6,7,8-hexahydro-N,N-dimethyl-(5 and/or 6-propyl)-3-phenyl-8-phenylmethylene-cyclohepta[c]pyrazole-2(3H)-propanamine, maleate salt,
3a,4,5,6,7,8-hexahydro-N,N-dimethyl-(5 and/or 6-t-butyl)-3-phenyl-8-phenylmethylene-cyclohepta[c]pyrazole-2(3H)-propanamine, maleate salt,
3a,4,5,6,7,8-hexahydro-N,N-dimethyl-(4 and/or 7-methyl)-3-phenyl-8-phenylmethylene-cyclohepta[c]pyrazole-2(3H)-propanamine, maleate salt,
3a,4,5,6,7,8-hexahydro-N,N-dimethyl-(4 and/or 7-ethyl)-3-phenyl-8-phenylmethylene-cyclohepta[c]pyrazole-2(3H)-propanamine, maleate salt, and
3a,4,5,6,7,8-hexahydro-N,N-dimethyl-(5 and/or 6-methyl)-3-(4-chlorophenyl)-8-[(4-chlorophenyl)methylene]-cyclohepta[c]pyrazole-2(3H)-propanamine, maleate salt.

EXAMPLE 18

3a,4,5,6,7,8-Hexahydro-3-phenyl-8-(phenylmethylene)-cyclopenta[c]pyrazole-2(3H)-ethanamine, oxalate salt a. 3a,4,5,6,7,8-Hexahydro-3-phenyl-8-(phenylmethylene)-cyclopenta[c]pyrazole-2(3H)-ethanol A suspension of 2,7-bis(phenylmethylene)cycloheptanone in methanol is treated with (2-hydroxyethyl)hydrazine. The mixture is heated and the resulting solution is refluxed for 4 hours, cooled, and the bulk of the methanol is evaporated. The resulting alcohol is triturated with ether, cooled overnight, filtered, and dried in vacuo to yield the titled product.

b. 3a,4,5,6,7,8-Hexahydro-3-phenyl-8-(phenylmethylene)-cyclopenta[c]pyrazole-2(3H)-ethanamine, oxalate salt The alcohol from part (a) is converted to the tosylate by treatment with p-toluenesulfonyl chloride in pyridine. The tosylate is reacted with ammonia and treated with a solution of oxalic acid in MeCN as described in example 1a yielding 3a,4,5,6,7,8-hexahydro-3-phenyl-8-(phenylmethylene)-cyclopenta[c]pyrazole-2(3H)-ethanamine, oxalate salt.

EXAMPLES 19–22

Following the procedure of example 18 but substituting the following alkylamines for the ammonia
methylamine
ethylamine
n-propylamine
t-butylamine
one obtains the following:

3a,4,5,6,7,8-hexahydro-N-methyl-3-phenyl-8-(phenylmethylene)-cyclopenta[c]pyrazole-2(3H)-ethanamine, oxalate salt;
3a,4,5,6,7,8-hexahydro-N-ethyl-3-phenyl-8-(phenylmethylene)-cyclopenta[c]pyrazole-2(3H)-ethanamine, oxalate salt;

3a,4,5,6,7,8-hexanhydro-N-(n-propyl)-3-phenyl-8-(phenylmethylene)-cyclopenta[c]pyrazole-2(3H)-ethanamine, oxalate salt; and 3a,4,5,6,7,8-hexahydro-N-(t-butyl)-3-phenyl-8-(phenylmethylene)-cyclopenta[c]pyrazole-2(3H)-ethanamine, oxalate salt.

EXAMPLES 23–36

Following the procedure of example 1 but substituting the hydrazine shown in column A for the 3-dimethylaminopropylhydrazine the products shown in column B are obtained.

| Ex. | Col. A | Col. B |
|---|---|---|
| 30 | 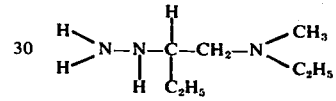 | 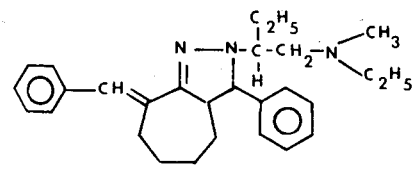 |
| 31 | 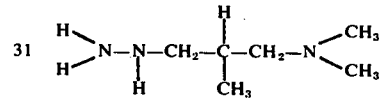 | 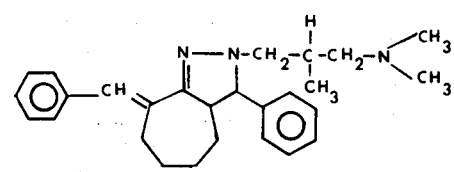 |
| 32 | 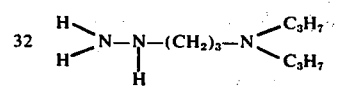 | 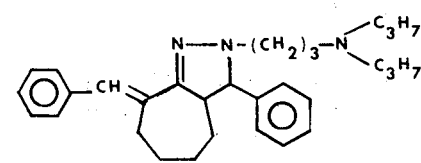 |
| 33 | 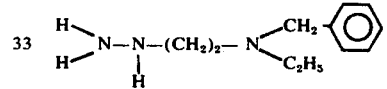 | 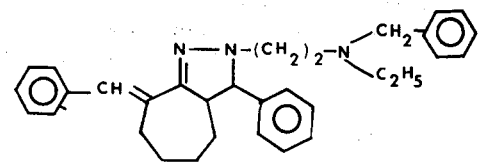 |
| 34 | 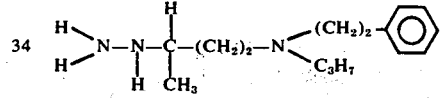 | 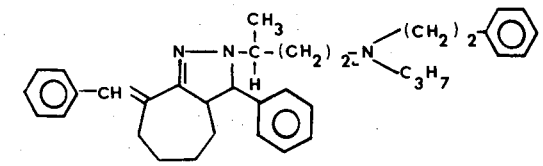 |
| 35 | 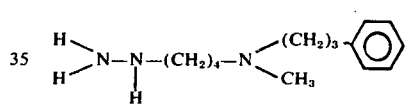 | 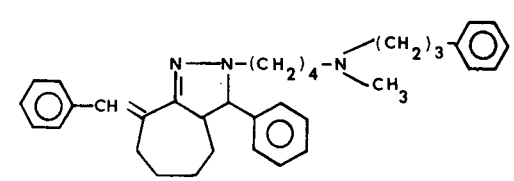 |

| Ex. | Col. A | Col. B |
|---|---|---|
| 36 | 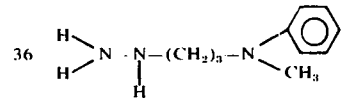 | 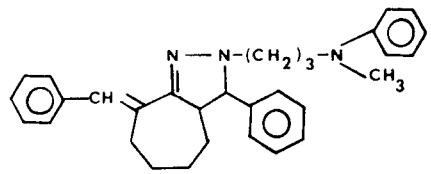 |

EXAMPLE 37

3a,4,5,6,7,8-Hexahydro-N,N-dimethyl-3-phenyl-8-(phenylmethylene)-cyclopenta[c]pyrazole-2(3H)-propanamine, methochloride A solution of the base from example 1b in acetonitrile is cooled and treated with methyl chloride. The solution is allowed to stand for one day and the solvent is evaporated to give 3a,4,5,6,7,8-hexahydro-N,N-dimethyl-3-phenyl-8-(phenylmethylene)-cyclopenta[c]pyrazole-2(3H)-propanamine, methochloride.

EXAMPLE 38

3a,4,5,6,7,8-Hexahydro-N,N-dimethyl-3-phenyl-8-(phenylmethylene)-cyclopenta[c]pyrazole-2(3H)-propanamine, N-oxide A solution of the free base of example 1b in methanol is treated with two equivalents of 30% $H_2O_2$. The solution is allowed to stand for two days and the solvent is removed under reduced pressure to give 3a,4,5,6,7,8-hexahydro-N,N-dimethyl-3-phenyl-8-(phenylmethylene)-cyclopenta[c]pyrazole-2(3H)-propanamine, N-oxide.

What is claimed is:

1. A compound of the formula:

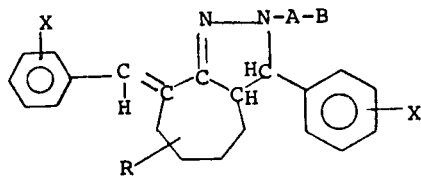

wherein X is selected from the group consisting of hydrogen, chloro, fluoro, lower alkyl, lower alkoxy, and trifluoromethyl; R is selected from the group consisting of hydrogen and lower alkyl; A is straight or branched chain alkylene of 1 to 8 carbons; B is selected from the group consisting of —$NH_2$,

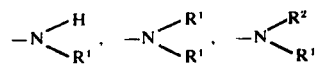

wherein $R^1$ is lower alkyl and $R^2$ is phenyl or phenyl-lower alkyl; and an acid addition or quaternary salt or N-oxide thereof.

2. The compound of claim 1 wherein X is selected from the group consisting of hydrogen, chloro, fluoro, lower alkyl of 1 to 4 carbon atoms, lower alkoxy of 1 to 4 carbon atoms, and trifluoromethyl; R is selected from the group consisting of hydrogen and lower alkyl of 1 to 4 carbon atoms; A is straight or branched chain alkylene of from 2 to 5 carbon atoms; $R^1$ is lower alkyl of 1 to 4 carbon atoms; and $R^2$ is selected from the group consisting of phenyl, benzyl and phenethyl.

3. The compound of claim 2 wherein R is hydrogen.

4. The compound of claim 3 wherein X is hydrogen or chlorine; A is —$(CH_2)_2$— or —$(CH_2)_3$—; and B is

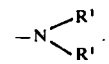

5. The compound of claim 4 wherein X is hydrogen, A is —$(CH_2)_3$— and B is

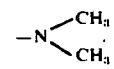

6. The compound of claim 5 having the name 3a,4,5,6,7,8-hexahydro-N,N-dimethyl-3-phenyl-8-(phenylmethylene)-cyclohepta[c]pyrazole-2(3H)-propanamine, maleate salt.

* * * * *